United States Patent [19]

Montoro et al.

[11] Patent Number: 4,812,482

[45] Date of Patent: Mar. 14, 1989

[54] APPLICATION OF α-[[(2-HYDROXY-1, 1-DIMETHYL-ETHYL) AMINE] METHYL] BENZENE METHANOL HYDROCHLORIDE (EL-508) AS A DRUG WITH ANTIINFLAMMATORY ACTION

[75] Inventors: Fernando Montoro; Jose Calatayud; Manuel Luna, all of Madrid, Spain

[73] Assignee: Especialidades Latinas Medicamentos Universales, S.A. (Elmu, S.A.), Madrid, Spain

[21] Appl. No.: 84,179

[22] Filed: Aug. 12, 1987

[51] Int. Cl.$^4$ ............................................. A61K 31/135
[52] U.S. Cl. .................................................. 514/649
[58] Field of Search ....................................... 514/649

Primary Examiner—Stanley J. Friedman
Attorney, Agent, or Firm—Sherman Levy

[57] ABSTRACT

An application of α-[[(2-hydroxy-1, 1-dimethyl-ethyl) amine] methyl] benzene methanol hydrochloride (EL-508), as a compound with antiinflammatory action, as well as the different pharmaceutical compositions in which the referred compound is the active principle and its use in therapeutics as an antiinflammatory drug.

7 Claims, No Drawings

APPLICATION OF α-[[(2-HYDROXY-1, 1-DIMETHYL-ETHYL) AMINE] METHYL] BENZENE METHANOL HYDROCHLORIDE (EL-508) AS A DRUG WITH ANTIINFLAMMATORY ACTION

FIELD OF THE INVENTION

The present invention relates to therapeutical applications, and more particularly to the application of α-[[(2-hydroxy-1, 1-dimethyl-ethyl) amine]methyl]benzene methanol hydrochloride (EL-508) as a drug with antiinflammatory action.

BACKGROUND OF THE PRESENT INVENTION

The present invention is directed to new therapeutical applications, and more particularly to a therapeutical application with antiinflammatory action.

The present invention in particular is directed to a therapeutical application of α-[[(2-hydroxy-1, 1-dimethyl-ethyl) amine]methyl]benzene methanol hydrochloride (EL-508) as a drug with antiinflammatory action.

DESCRIPTION OF THE INVENTION

The purpose of the present invention is the application of α-[[(2-hydroxy-1, 1-dimethyl-ethyl) amine]methyl]benzene methanol hydrochloride (EL-508) as a drug with antiinflammatory action, as well as the different pharmaceutical compositions in which the referred compound is the action and its use in therapeutics as an antiinflammatory drug.

Considering inflammation as a normal physiological response to an aggression and not as a pathological phenomenon, this product in the use of antiinflammatory substances inhibiting the reorganic activity because this sometimes excessively upsets the patients functionality or comfort. Further, the use of these drugs is adapted to minimize their undesirable effects deriving of their anti-defensive action.

Further, primary therapeutics will have to fight against post-lesions oedemas and against primary inflammation, while simultaneously suppressing pain, periarticular fibrosis, amiotrophy and local calcic mutations and the like.

Also, the topical use of antiinflammatory drugs in acute oedematous process brings on in many cases a revulsive and irritant effect which may be contraindicated with the anti-flogistic activity itself this effect being intensified in the case of open tissular lesions.

Furthermore, in certain cases, the local therapeutics of inflammatory processes have used drugs with well-known systematic antiinflammatory properties, but which structures or physico-chemical characteristics do not allow them to go through skin corneum thereby reducing their pharmacological activity potential due to topographical impossibility.

In looking for a drug with intense topical antiinflammatory activity and good tolerance, the compound α-[[(2-hydroxy-1, 1-dimethyl-ethyl) amine]methyl]benzene methanol hydrochloride was syntheiszed and developed, and its chemical structure is completely different from that of conventional non-steroid anti-inflammatory drugs. This drug proved to possess a great antiinflammatory activity both in use by the oral and topical route, and was demonstrated in several experiments of acute inflammation. In all the cases, this effect was higher than the referenced products used (fenylbutazone, pyridil-3-methylamine salicilate, benzidamine salicilate, etc.)

It is to be emphasized that the antiinflammatory effect is direct, without central or hormaonal stimulus, as it has been demonstrated in trials carried out on adrenalectomized rats.

Also, in experimental chronic inflammatory processes, α-[[(2-hydroxy-1, 1-dimethyl-ethyl) amine]methyl]benzene methanol hydrochloride, demonstrated its activity on primary inflammatory phenomena.

In addition, in all the administration routes, the compound proved to be highly active against capillary permeability increases, induced by xylol and chloroform. This stabilizing effect of vascular permeability did not modify at all peripheral blood flow, that is, it does not produce peripheral vasodilation nor vasoconstruction.

It appears that this activity on capillary permeability is responsible for the pharmacological action in the first phases of the inflammatory process.

Further, the tolerance of the compound was tested by systematic routes, after prolonged daily administrations which reached up to 1250 mg/kg of product and by topical routes, in which the compound administered in solution was perfectly tolerated in the skin, genital and conjunctival mucous membranes, both in animals and human volunteers.

In summary, α-[[(2-hydroxy-1, 1-dimethyl-ethyl) amine]methyl]benzene methanol hydrochloride, can be defined as a new molecule, structurally unrelated to other antiinflammatories, with an intense antiedematous action in acute processes both by systematic and topical routes, with a strong effect on capillary permeability increases, a slight ulcerogenic action and no undesirable side effects. Its systematic and topical tolerance has been demonstrated. Further, its acute and chronic toxicity was very low. All of these characteristics prove that α-[[(2-hydroxy-1, 1-dimethyl-ethyl) amine]methyl]benzene methanol hydrochloride is a useful drug in the treatment of acute inflammatory processes as well as in the primary inflammatory phenomena of chronic pressure.

The characteristics of the compound are as follows:
Empiric formula:
$C_{12}H_{19}NO_2 \cdot HCl$
Elemental analysis:
C. 58.63%, H. 8.21%, N. 5.70%, Cl. 14.43%
Mol. Wt. : 245,62
Melting point: 129°–130° C.
Infrared spectrum (K Br):
3470, 3000, 1600, 1060, 760, 695 cm-1
UV spectrum (HCl 0,1N):
251, 257, 262 nm
Optical rotation: Inactive.

It is to be emphasized that the present invention possesses certain important differences and advantages not previously described in any publication or otherwise known. The experiments carried out in laboratories have proved the antiinflammatory action of this product, by the oral route or topical application. In order to evaluate the therapeutic interest, its pharmacological properties have been defined in comparison to other well-known drugs. The studies were carried out with the product under the hydrochloride form, this salt being called EL-508.

Further, attention is directed to the following table which shows the antiinflammatory activity by the oral route on different acute experimental oedemas induced in a rat through various phlogogenous agents. $ED_{50}$ are indicated, these corresponding to the dose which produces 50% of oedema inhibition.

| ED$_{50}$ mg/kg | Carrageenin | Kaolin | Ovoalbumin | Formol | Carrageenin abscess |
|---|---|---|---|---|---|
| EL-508 | 29,8 | 44,9 | 16,7 | 21,7 | 9,4 |
| Fenilbutazone | 200 | — | Inactive | — | 80 |

Further, the product proved to be more active than the reference drugs on carrageenin and formalin-induced peritonitis, after oral administration of equal doses of all of them (100 mg/Kg).

The following table shows the comparative results of this experiment, expressed in percentage of inhibition:

|  | Carrageenin perit. | Formalin perit. |
|---|---|---|
| EL-508 | 70,8% | 28,1% |
| Oxyphenylbutazone | 58,8% | 7,5% |
| Benzidamine HCl | 31,3% | 15,6% |

Further, it is to be noted that the antiinflammatory activity of EL-508, after its topical application, in 6% aqueous or alcoholic solutions in acute experimental processes, is summarized in the following table in comparison to 6% benzidamine HCl as a reference drug:

|  | Inhibition % of oedemas | | | |
|---|---|---|---|---|
|  | carrageenin | ovoalbumin | Kaolin | Croton oil |
| EL-508 | 48 | 40,6 | 47,5 | 30 |
| Benzidamine HCl | 7 | 42,0 | 0 | 44 |

In addition, EL-508 in solution for topical application proved to have a stabilizing action on vascular permeability and reduced by 50% the extravasation this being induced either by xylol or chloroform. In these tests Benzidamine HCl lacked action.

Further, the aqueous solution of the product was well tolerated either on the skin or on conjunctive and vaginal mucous membranes after repeated applications.

Toxicity

The following table shows the LD$_{50}$ of EL-508 in different application routes and animal species:

| Species | Administration route | LD$_{50}$ mg/kg |
|---|---|---|
| Mouse | p.o. | 1025 |
|  | i.v. | 79 |
|  | i.p. | 295 |
| Rat | p.o. | 2080 |
|  | i.v. | 80 |
|  | i.p. | 350 |

Further, it is to be noted that chronic toxicity studies carried out on rats and dogs over six months, p.o. at doses up to 100 mg/kg/day, showed no undesirable effects attributable to the product.

Further, EL-508 always proved to be a drug strongly acting on the primary responses of inflammatory processes. As a result of its low acute and chronic toxicity, the therapeutic indices are considerably higher than for the reference compounds in the different experimental models which means that EL-508 potentially offers a large scale of pharmaceutical applications.

When used as a drug, the compound of the present invention and its salts can be be administered by oral or topical routes, either alone or in the adequate pharmaceutical combination such as tablets, powders, aerosol solutions, ointments and the like.

CLINICAL TRIALS

Several clinical trials have been carried out with different pharmaceutical compositions with α-[[(2-hydroxy-1, 1-dimethyl-ethyl) amine]methyl]benzene methanol hydrocholride (EL-508) as active principle. In the 6% aerosol pharmaceutical composition the therapeutic action was studied in muscular-ligamentous pathological processes: luxations, sprains, contusions and the like. The results indicated a therapeutic action higher than pyiridil-3-methyl amine salicylate and placebo.

Further, as to the pharmaceutical forms of solutions for vaginal applications at 5% and 0,2% various clinical trials were performed in patients with vaginitis of unknown ethiology or atrophic vaginitis and specific infectious vaginitis. The compound EL-508 proved to be more effcent in these indications than iodic povidone and placebo.

Further, the pharmaceutical preparations for oral administration can also contain besides the active substance, one or several pharmaceutically accepted excipients. The pharmaceutical preparations for topical administration are prepared as usual and these can contain in addition to the active principle, solvents, solubilizing, dispersing, conserving or flavoring agents.

The following are given as examples of pharmaceutical compositions:

| (a) Tablets, prepared according to the usual methods. | |
|---|---|
| Composition: | |
| α-[[(2-hydroxy-1, 1-dimethyl-ethyl) amine]methyl] benzene methanol hydrochloride | 100 mg |
| Corn starch | 100 mg |
| Microcrystalline cellulose | 60 mg |
| Talc | 10 mg |
| Magnesium stearate | 5 mg |

| (b) Aerosol solution for topical application, 2 to 4 times a day. | |
|---|---|
| Composition: | |
| α-[[(2-hydroxy-1, 1-dimethyl-ethyl) amine]methyl] benzene methanol hydrochloride | 4 mg |
| Propyleneglycol | 2,5 mg |
| Flavoring agents | q.s. |
| Ethyl alcohol in quantity required for | 25 ml |
| Propellant | 15 ml |

| (c) Vaginal solution (direct application). | |
|---|---|
| Composition: | |
| α[[(2-hydroxy-1, 1-dimethyl-ethyl) amine]methyl], benzene methanol hydrochloride | 0,2 g |
| Propyleneglycol | 10 g |
| Preservative agents | q.s. |
| Flavoring agents | q.s. |
| Water in quantity required for | 100 ml |

Attention is directed to the following further examples:

VAGINAL SOLUTION

Indications: Leucorrhoeas, vaginitis, vulvovaginitis, cervicovaginitis, cervicitis, all of them unspecific or from mixed etiology.

Dosage: One intravaginal application (10-20mg) every 12 hours.

AEROSOL

Indications: Inflammatory and traumatic processes, due to bony fractures, distorsions, contusions and luxations. Tendinitis and tendosinovitis. Local coadjuvant of musculary inflammations and lumbago treatment.

Dosage: 3 or 4 applications per day, covering the injured area.

TABLETS

Indications: Acute inflammatory processes in gynecology, ophtalmology, urology, pediatrics, etc. Post-traumatic and post-operation inflammatory processes and tumefaction; in sport and labor medicine, articulary, bony as well as tender parts, traumatisms.

Dosage: 1 tablet of 100 mg, twice or three times a day.

While several embodiments of the present inventions have been illustrated herein in particular detail, it will be understood that variations and modifications may be effected without departing from the spirit and scope of the novel concepts of this invention.

What is claimed:

1. A method for antiinflammatory treatment comprising:
   administering to a subject having inflammation, a therapeutically effective amount of α-[[(2-hydroxy-1, 1-dimethyl-ethyl) amine]methyl]benzene-methanol hydrochloride having a formula:

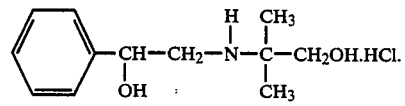

2. The method of claim 1 wherein said administering to said subject is by oral injestion.

3. The method of claim 2 wherein said therapeutically is about 100 mg, 2 or 3 times per day.

4. The method of claim 1 wherein said administering is by topical application.

5. The method of claim 4 wherein said therapeutically effective amount is a 6 percent concentration in an aqueous or an alcoholic solution.

6. The method of claim 1 wherein said administering is by vaginal irrigation.

7. The method of claim 6 wherein said therapeutically effective amount is a solution having a concentration of 5.0 percent.

* * * * *